(12) United States Patent
Dueppenbecker et al.

(10) Patent No.: US 9,335,425 B2
(45) Date of Patent: May 10, 2016

(54) MODELLING OF TOF-DOI DETECTOR ARRAYS

(71) Applicant: KONINKLIJKE PHILIPS N.V., Eindhoven (NL)

(72) Inventors: Peter Michael Jakob Dueppenbecker, Aachen (DE); Torsten Solf, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 37 days.

(21) Appl. No.: 14/349,103

(22) PCT Filed: Oct. 12, 2012

(86) PCT No.: PCT/IB2012/055544
§ 371 (c)(1),
(2) Date: Apr. 2, 2014

(87) PCT Pub. No.: WO2013/054300
PCT Pub. Date: Apr. 18, 2013

(65) Prior Publication Data
US 2014/0231655 A1 Aug. 21, 2014

Related U.S. Application Data

(60) Provisional application No. 61/546,101, filed on Oct. 12, 2011.

(51) Int. Cl.
*G01T 1/20* (2006.01)
*G01T 1/29* (2006.01)
*A61B 6/03* (2006.01)

(52) U.S. Cl.
CPC ............... *G01T 1/20* (2013.01); *G01T 1/2002* (2013.01); *G01T 1/2985* (2013.01); *A61B 6/037* (2013.01)

(58) Field of Classification Search
CPC ........ G01T 1/20; G01T 1/2002; G01T 1/2985
See application file for complete search history.

(56) References Cited

U.S. PATENT DOCUMENTS

| 4,675,526 | A | 6/1987 | Rogers et al. |
| 4,831,263 | A | 5/1989 | Yamashita |
| 4,945,241 | A | 7/1990 | Yamashita et al. |
| 7,476,864 | B2 | 1/2009 | Benlloch Baviera et al. |
| 7,567,646 | B2 | 7/2009 | Buchinsky |
| 2004/0178347 | A1 | 9/2004 | Murayama et al. |
| 2005/0087693 | A1 | 4/2005 | Sumiya et al. |
| 2010/0012846 | A1 | 1/2010 | Wang |
| 2011/0001049 | A1* | 1/2011 | Shibuya et al. ............... 250/362 |

(Continued)

OTHER PUBLICATIONS

Degenhardt, C., et al.; The Digital Silicon Photomultiplier—A Novel Sensor for the Detection of Scintillation Light; 2009; IEEE Nucl. Scien. Symp. Conf. Record; pp. 2383-2386.

(Continued)

*Primary Examiner* — David Porta
*Assistant Examiner* — Mindy Vu

(57) ABSTRACT

The invention is directed to several crystal arrangements for time-of-flight (ToF) positron emission tomography (PET) with depth of interaction (DOI) encoding for high spatial, energy and timing resolution. Additionally, several implementations of the ToF-DOI PET detector arrays are proposed with related measurements which all show that no timing degradation is visible in the used setup for first photon trigger for digital silicon photo multipliers (dSiPMs).

14 Claims, 9 Drawing Sheets

(56) References Cited

U.S. PATENT DOCUMENTS

2011/0101229 A1 5/2011 Inadama et al.
2011/0192982 A1 8/2011 Henseler et al.

OTHER PUBLICATIONS

Frach, T., et al.; The Digital Silicon Photomultiplier—Principle of Operation and Intrinsic Detector Performance; 2009; IEEE Nucl. Scien. Symp. Conf. Record; pp. 1959-1965.

Gagnon, D., et al.; Maximum likelihood positioning in the scintillation camera using depth of interaction; 1993; IEEE Trans. on Medical Imaging; 12(1)101-107.

Nishikido, F., et al.; Spatial resolution evaluation with a pair of two four-layer DOI detectors for small animal PET scanner: jPET-RD; 2008; Nucl. Inst. and Meth. A; No. 584; pp. 212-218.

Orita, N., et al.; Three-dimensional array of scintillation crystals with proper reflector arrangement for a depth of interaction detector; 2004; Nuc. Science Symposium Conf. Record; V. 4; pp. 2391-2395.

St. James, S., et al.; Experimental characterization and system simulations of depth of interaction PET detectors using 0.5 mm and 0.7 mm LSO arrays; 2009; Phys. Med. Biol.; 54(14)4605-4619.

Yang, Y., et al.; Investigation of Depth of Interaction Encoding for a Pixelated LSO Array with a Single Multi-Channel PMT; 2009; IEEE Trans. Nucl. Sci.; 56(5)2594-2599.

* cited by examiner

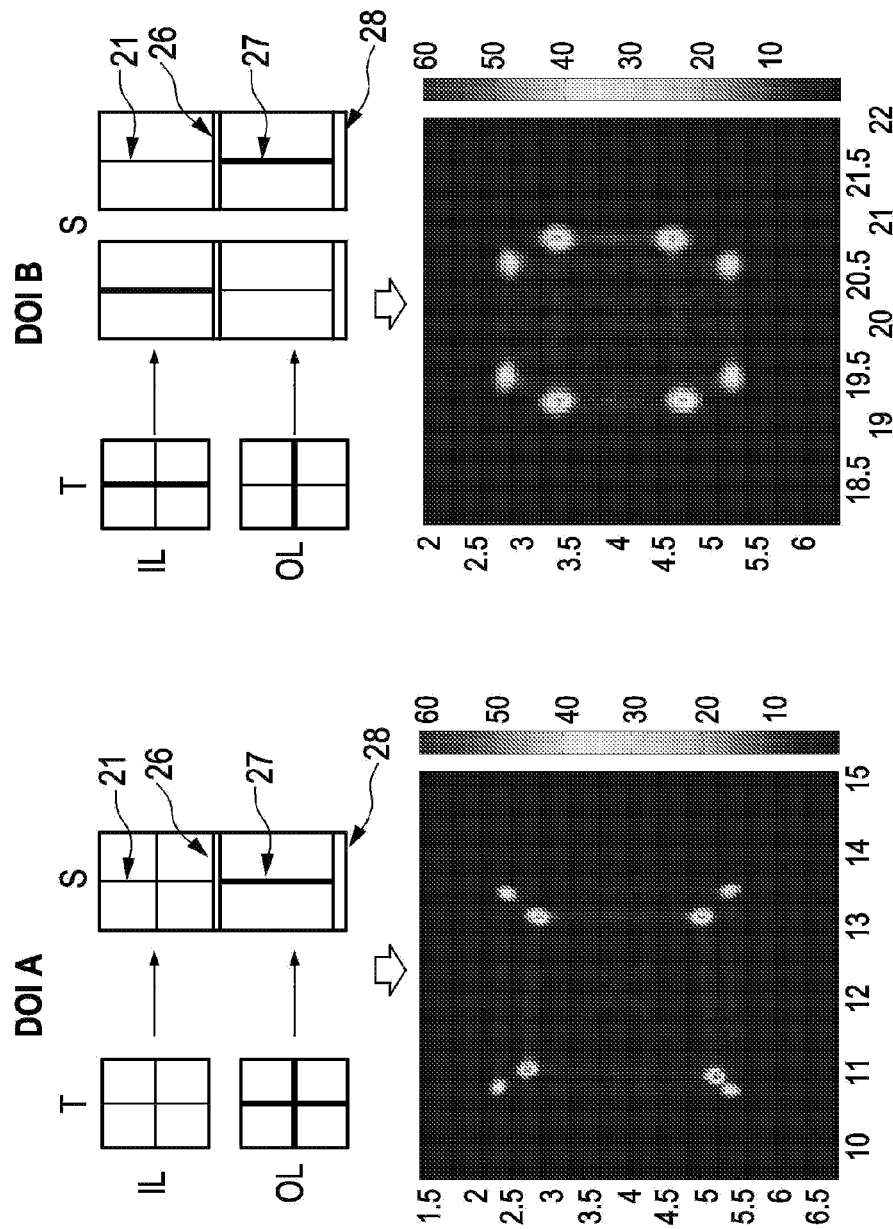

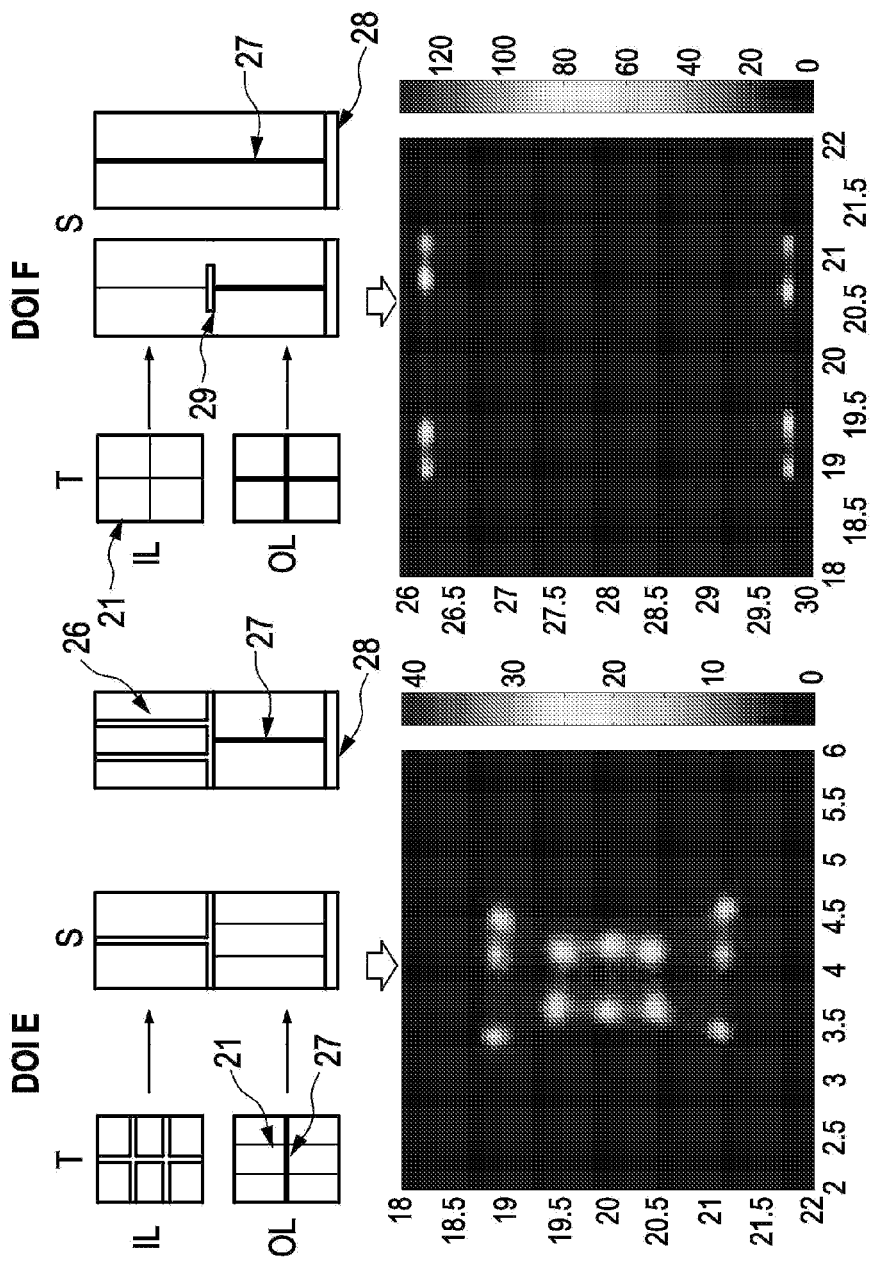

MODELLING OF TOF-DOI DETECTOR ARRAYS

CROSS REFERENCE TO RELATED APPLICATIONS

This application is a national filing of PCT application Serial No. PCT/IB2012/055544, filed Oct. 12, 2012, published as WO 2013/054300 A2 on Apr. 18, 2013, which claims the benefit of U.S. provisional application Ser. No. 61/546,101 filed Oct. 12, 2011, which is incorporated herein by reference.

FIELD OF THE INVENTION

The invention relates to the field of positron emission tomography (PET) systems with depth-of-interaction (DOI) and time-of-flight (ToF) encoding.

BACKGROUND OF THE INVENTION

Recent advances in the field of medical imaging have greatly facilitated the transition from technologies used to accurately image structures inside the human body to technologies sensitive enough to provide functional and biological information at the cellular and the molecular level. PET is considered to be one of the most sensitive in-vivo molecular imaging modalities despite its significantly inferior spatial resolution compared to imaging modalities such as computed tomography (CT) and magnetic resonance imaging (MRI). The improvement of PET detector technology is an active field of research and efforts are focused on addressing the limits in spatial resolution and sensitivity achieved in PET.

FIG. 1 shows a schematic block diagram of a PET imaging system in which the present invention can be implemented. In PET imaging, positrons are emitted from a radiopharmaceutically doped organ or tissue mass of interest of a patient 100. The positrons combine with electrons and are annihilated and, in general, two gamma photons which travel in diametrically opposite directions are generated upon that annihilation. A PET acquisition is based on the coincident detection of many pairs of simultaneous anti-parallel photons following the annihilation of the positron. The detection is performed by a detector 110 which comprises a plurality of detector element pairs which are placed around the imaged object, typically in a ring geometry. Opposing crystal detectors, which each scintillate upon being struck by a gamma photon, are used to detect the emitted gamma photons. Coincidence detection may be performed by a coincidence processing unit 120. By identifying the location of each of two essentially simultaneous gamma interactions as evidenced by two essentially simultaneous scintillation events, a line in space along which the two gamma photons have traveled (a "line of response," or "LOR") can be determined. The LORs associated with many million gamma interactions with the detectors are calculated and reconstructed to generate an image of the organ or tissue mass of interest in an image reconstruction unit 130. Thus, in PET imaging systems the detection of incident radiation is achieved by a two-step conversion of the annihilation photon energy to visible light in a scintillation material and to electric charge in the detector 110.

Time-of-flight PET (ToF-PET) is an advance over traditional PET that exploits the arrival time difference in detection of two photon events and correlates it to the position of the annihilation point with respect to the center of the field of view (FoV). The flight time difference between the two detected photon events is in a first approximation related to the object position along the line connecting the two detector elements: dx=c/2dt. The benefit in image quality depends on the time-stamp jitter. The effect is fairly dramatic, as each time the jitter is reduced by a factor of two, the patient acquisition time can also be reduced by a factor of two.

There are several types of photo detectors available: The first family of photo detectors covers the vacuum tubes: Photomultiplier tubes (PMTs) with a fairly large detector area of several square centimeters, and multi-anode PMTs which provide position information of a few millimeters, allowing pixilation in the millimeter range.

The photomultiplier tube (PMT) is a photo-detector type commonly used for scintillator readout in numerous applications including medical imaging. In ToF-PET, PMTs are often used for sub-nanosecond time resolution. The basic component of a PMT is a vacuum tube consisting of a photocathode, several electrodes called dynodes and an anode. The photocathode is a photo-sensitive electrode that emits charge (electrons) for a number of incident optical photons absorbed with a given quantum efficiency (QE). Between the cathode and the anode a bias voltage in the kV range is applied to facilitate the generated electron transport and amplification from the cathode to the anode. Under the influence of a high potential the generated electrons from the photocathode drift and successively encounter the dynode stages. At every dynode stage the incident electrons have gained sufficient energy to create secondary electron emissions from collisions with the dynode, thus resulting in a large electron cloud at the anode.

The second family of photo detectors is silicon based and incorporates either avalanche photo-diodes (APDs), analog or digital silicon photomultipliers (SiPMs) which are based on multi element avalanche photodiodes driven in Geiger Mode. All silicon detectors allow designs of PET/SPECT detectors with a small pixilation in the millimeter range. But only the analog and digital SiPMs (dSiPMs) allow sub nanosecond timestamping to exploit the benefits of ToF-PET.

Furthermore, silicon photomultipliers (SiPMs) have been introduced to address shortcomings of PMTs to realize smaller pixilation. A novel technological advance in the field of semiconductor photo-detectors has been recently developed and involves the integration within the SiPM sensitive area of basic processing electronics thus reducing the need for external processing electronics. Each micro-cell of the array is connected to an integrated counter (for extraction of energy information) and an integrated time to digital converter (TDC) for extraction of time information. This alternative SiPM design is known as "digital SiPM" or "dSiPM" and time resolutions as low as 150 ps full width at half maximum (FWHM) with LYSO readout have been reported.

In some of the earlier PET systems, gamma detectors could be used only to determine the location of gamma interaction with the detector in two dimensions, which gave rise to parallax errors. More particularly, a conventional two-dimensional measurement of the spatial location of a detected gamma ray absorption event in the scintillating crystal is limited to a two-dimensional point in the X, Y plane of the crystal. The paralax error is a key limiting factor in image resolution, especially for larger patients. This reduces the detectability of small lesions in the outer field of view.

The depth of interaction (DOI) is an important parameter when applied to imaging detector geometries where the directions from which incident gamma rays impinge upon the crystal are not all substantially normal to the crystal surface. If incident gamma rays intersect the crystal from directions not normal to the crystal, the unknown depth of interaction of those gamma rays within the crystal will result in an additional uncertainty in the measured position of the interaction because of the parallax effect, if only a two dimensional (i.e., X, Y) spatial location is calculated for such an absorption event. A detailed explanation of the importance of and the problems associated with the DOI is provided in "Maximum Likelihood Positioning in the Scintillation Camera Using Depth of Interaction," D. Gagnon et al., IEEE Transactions on Medical Imaging, Vol. 12, No. 1, March 1993, pp. 101-107.

Thus, parallax errors could be reduced by using DOI information to increase the spatial resolution of the system, i.e., to provide the location of gamma interaction in three dimensions in space. In this regard, some PET scanners are able to provide DOI information using axially stacked scintillators which use a pulse shape discrimination method to minimize parallax error. For this example, a DOI detector includes at least two different types of crystal materials, each of which has a different scintillation decay constant, arranged in multiple layers. By discriminating based on the pulse shape, one can differentiate between interaction events that take place in either crystal layer. The layers are subdivided into individual pixel elements to discriminate where within a given layer the interaction has taken place, and reflector partitions may be provided between the crystal elements to better identify the crystal elements in which the interactions take place. Furthermore, a light guide, with or without grooves, and photosensors (e.g. PMTs or other solid state devise) are employed on a single side of the detector in conventional manner.

FIG. 2 shows a diagram of radial spatial resolution vs. radial distance with a simulated resolution across axial field of view in case of a double layer DOI detector ("2 DOI") and a non-DOI detector ("0 DOI"). So far, conventional PET systems ("0 DOI") suffer from DOI problems and the resolution deteriorates for larger objects across the axial field of view. Therefore, lesions in the outer contour of the human body (especially large patients) like cancerous lymph nodes cannot be detected with the same image resolution as objects in the body centre. Multi layer DOI detectors ("2 DOI") could reduce this effect drastically, increase the small lesion detectability and increase life expectancy of the patients.

FIG. 3 shows a schematic example of a double layer DOI detector with shifted pixels in horizontal direction (i.e. x-direction of the coordinate system shown in FIG. 1) for detecting incident gamma photons xx. The double layer DOI detector with single sided readout and depth encoding is composed of two layers of scintillator arrays 22, 24. Each layer is composed of a plurality of polished crystals 10 with a small pitch (e.g. about 1 mm). This assembly may be mounted with a light guide 25 onto a dSiPM 28 array with a small pitch (e.g. about 4 mm). The width of the detector block may be about 32 mm. However, such multi layer DOI encodings suffer from deterioration in timing resolution, as the light is spread over a larger area. This is especially problematic for analog SiPM readout due to their much higher noise floor than photo multiplier tubes (PMTs), which is 1000-10000 times higher per unit area. Therefore, excellent timing can only be achieved when a small sensitive area (at low sensor temperature) is used. The digital SiPMs overcome this problem as individual microcells can be deactivated to reduce the noise floor by several decades.

SUMMARY OF THE INVENTION

It is an object of the invention to provide detection with DOI encoding without losing timing resolution or energy resolution.

This object is achieved by a detector device as claimed in claim 1 and by an imaging system as claimed in claim 15.

Accordingly, by providing the optical compartments (e.g. light tight compartments) and suitably setting the coupling parameters, a detector with DOI encoding and minimal geometric spread of the emitted scintillator light across the sensor surface with individual focal spots in the flood map can be achieved. This allows position encoding independent from the sensor pitch and size so as to achieve increased freedom in detector design.

According to a first aspect, the photo detector array may comprise a plurality of digital silicon photomultipliers. This measure reducing the need for external processing electronics and ensures enhanced time resolution.

According to a second aspect which may be combined with the first aspect, the detector device may further comprise a first light guide sandwiched between the second layer and the first layer and used for coupling the first and second layers, and a second light guide sandwiched between the photo detector array and the first layer and used for coupling the first layer and the photo detector array. The coupling with the light guides preserves high light output and provides the desired DOI information endoced in the spread of the light.

According to a third aspect which can be combined with any one of the first and second aspects, a pitch of the light tight compartments may be adapted to a sensor die pitch of the photo detector array. A die can house variable number of sensors (e.g. 1, 2, 4, 9, 16, . . . ). Thereby, it can be ensured that proper timestamping by one TDC or several TDCs is achieved.

According to a fourth aspect which can be combined with any one of the first to third aspects, the optical compartments may be adapted to provide vertical reflectors in the second layer and no reflectors in the first layer. More general, the optical compartments may be adapted to provide reflectors in a first or second direction in the second layer and no reflectors in the first layer, the first direction being perpendicular to the second direction. This detector setup is fairly simple and allows DOI in the lateral field of view.

According to a fifth aspect which can be combined with any one of the first to third aspects, the optical compartments may be adapted to provide reflectors in a first direction (e.g. x-direction) in the second layer and reflectors in a second direction (e.g. y-direction) in the first layer, wherein the first direction is perpendicular to the second direction. This detector setup is advantageous in that it uses asymmetry in vertical and horizontal spread to do encoding.

According to a sixth aspect which can be combined with any one of the first to fifth aspects, the coupling parameters may be set so that maximum light coupling is provided in the second layer and minimum light coupling is provided in the first layer, or so that minimum light coupling is provided in the second layer and maximum light coupling is provided in the first layer. Thereby, two simple ways of designing suitable coupling factors with similar energy and timing performance can be provided.

According to a seventh aspect which can be combined with any one of the first to sixth aspects, the optical compartments can be square or rectangular any multiple sensor pitch size (like 2*2, 2*3, 3*3, 3*4, . . . ) or independent from the sensor pitch.

According to an eighth aspect which can be combined with any one of the first to seventh aspects, the crystal pitch in any crystal layer (e.g. first or second or any additional layer) can be different from each other (like 2 mm in one layer and 3 mm in another layer).

According to a ninth aspect which can be combined with any one of the first to eighth aspects, the crystal pitch in any crystal layer can be different in a first (x) and second (y)

direction, (like 2 mm in x and 3 mm in y direction), wherein the first direction is perpendicular to the second direction.

According to a tenth aspect which can be combined with any one of the first to ninth aspects, more than two layers of scintillation crystals may be used in a stacked detector (e.g. 3 or 4 layers).

According to an eleventh aspect which can be combined with any one of the first to tenth aspects, crystal areas facing the photo detector array may be rectangular (e.g. 2 mm*3 mm).

Further advantageous embodiments are defined below.

BRIEF DESCRIPTION OF THE DRAWINGS

These and other aspects of the invention will be apparent from and elucidated with reference to the embodiments described hereinafter.

In the drawings:

FIG. 5 shows a flood map and a setup of a DOI detector device according to a first embodiment of the present invention;

FIG. 6 shows a flood map and a setup of a DOI detector device according to a second embodiment of the present invention

FIG. 9 shows a flood map of a setup of a DOI detector device according to a fifth embodiment of the present invention;

FIG. 10 shows a flood map of a setup of a DOI detector device according to a sixth embodiment of the present invention;

DETAILED DESCRIPTION OF EMBODIMENTS

Various embodiments are now described based on a ToF PET system with DOI encoding for high spatial, energy and time resolution.

According to some embodiments, a DOI detector device for the ToF PET system is provided with predefined performance characteristics. The proposed detector device provides DOI encoding without losing timing resolution or energy resolution. A minimal geometric spread of the emitted scintillator light can be achieved across the sensor surface with individual focal spots in the flood map (or flood image or flood histogram, based on the first moment calculation). In these designs, the DOI information can be estimated from the flood map (i.e. 2D crystal position map), which is calculated by the centroid of light dispersion on a SiPM sensor array. Because the centroid of light dispersion is shifted with the offset of crystal arrangement, the flood positions corresponding to crystals in all layers are separated in the flood image. This allows a position encoding independent from the sensor pitch and size allowing great freedom in the detector design.

Figure 1:
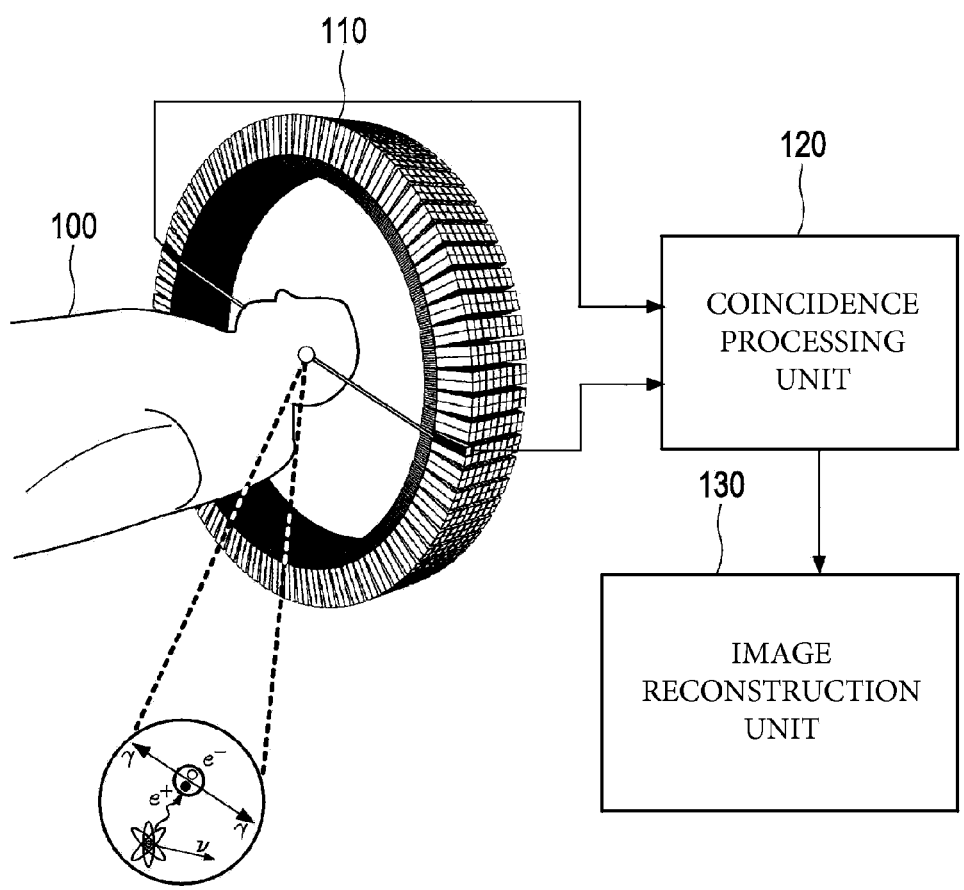
FIG. 1 shows a schematic block diagram of a PET imaging system in which the present indention can be implemented.
Figure 2:
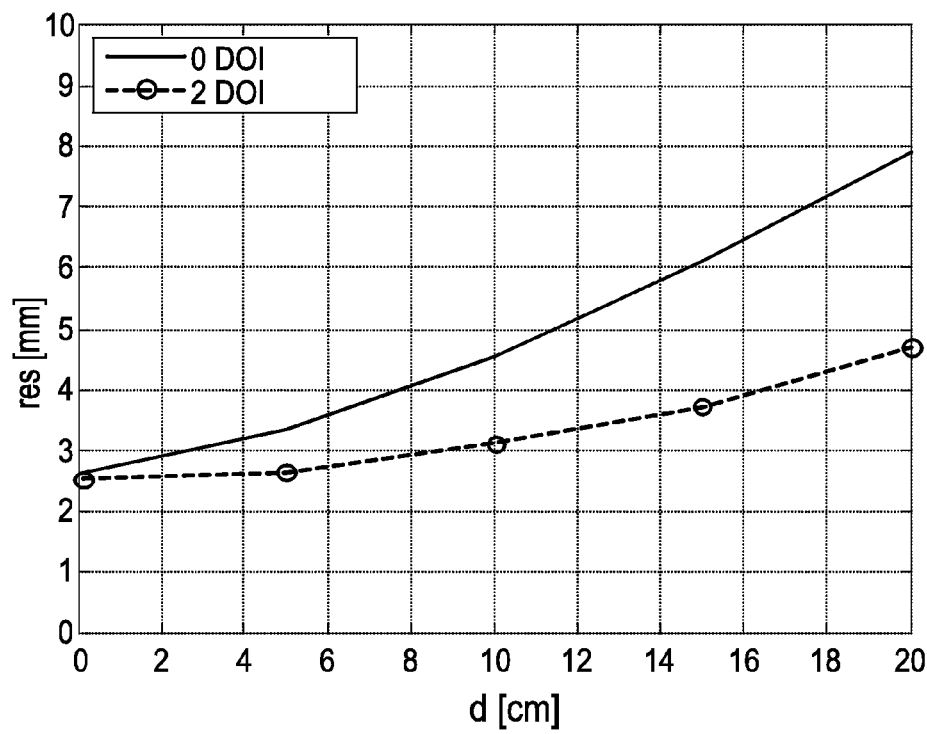
FIG. 2 shows a diagram indicating simulated resolution across axial field of view without and with a 2 layer DOI detector.
Figure 3:
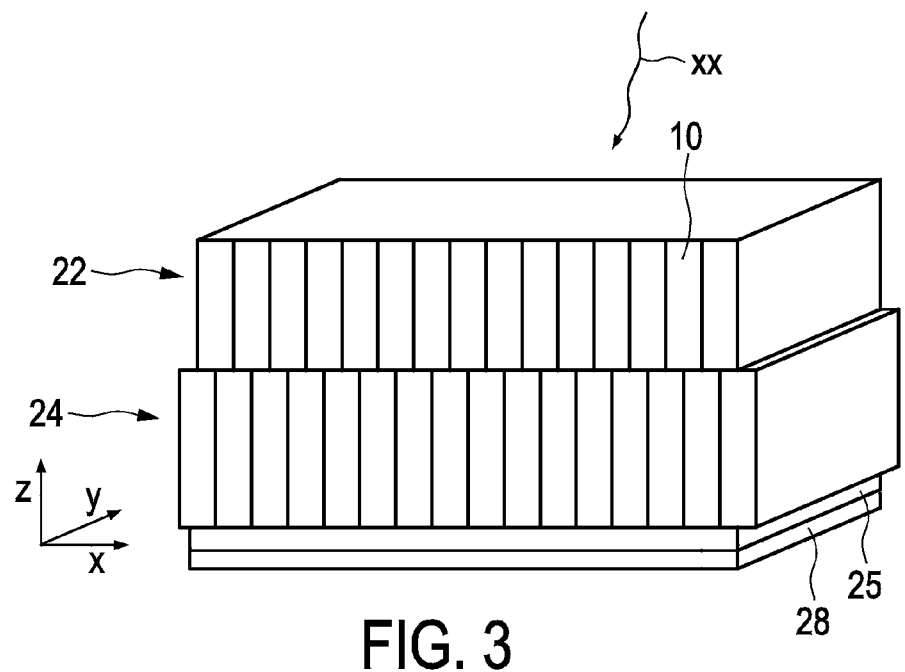
FIG. 3 shows a schematic structure of an application example of double layer DOI with shifted pixels in x and y direction.
Figure 4:
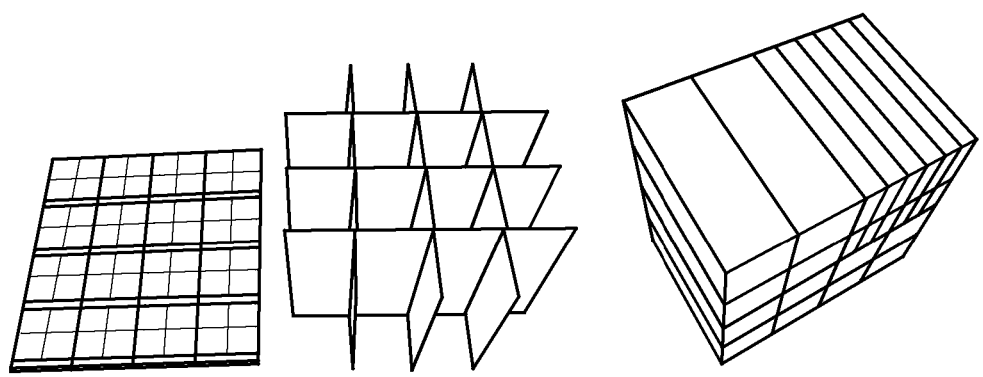
FIG. 4 shows specific parts of DOI detector device according to some embodiments of the present invention before mounting.

FIG. 4 shows a general example of components of a DOI detector device with dSiPM sensor (left), reflector grid (middle) and crystal array (right) according to some embodiments before mounting. Light tight compartments may be used which are larger than a crystal footprint but still small enough for excellent performance. Here, the compartment pitch may be tailored to the sensor die pitch which houses one TDC per die for timestamping. In some embodiments below a 8 mm pitch was used with reflective septa made out of a very light tight compound of a optical (dielectric or metal) mirror. The compartment pitch can be of course different as well as the type of reflector (specular or diffuse). Especially if more than one TDC is available within this pitch, the compartment size can be reduced in x and/or in y direction or both.

According to some embodiments, simple modelling of the location of the crystals within the local flood maps within the compartments is achieved. This allows a prediction and fine adjustment of the setup for different design goals with a variable number of DOI layers.

Most optical photons of the scintillation light undergo multiple reflections within the crystal before hitting a sensor element. The transfer function depends of several wavelength dependent factors including total reflection, diffuse reflection, specular reflection, reflection due to different refractive index between two materials like crystal and reflector, or crystal and optical glue, crystal and air, etc., surface treatment of the crystal (e.g. rough, polished, etc.), absorption within crystal, reflector, etc., slits, perforation of the reflector, lateral light guides and air, dust, etc. All these effects could be summarized in a general transfer function determining the light distribution on the sensors involved.

More specifically, suitable coupling factors can be designed by using maximum light coupling in the inner layer and minimum coupling in the outer layer, or by using minimum light coupling in the inner layer and maximum coupling in the outer layer. Both versions were tested and give similar energy or timing performance.

In the following, several embodiments are described in more detail based on their detector setups to show the variability of the proposed solution. The test equipment is based on dSiPMs on a sensor tile which gave a nominal timing resolution of 365 ps and energy resolution of 10.5% at room temperature for standard clinical crystals (3.8 mm*3.8 mm*22 mm) mounted as arrays. All experiments were performed with first photon trigger at room temperature. It is assumed that an improved sensor array will shift all timing numbers simultaneously.

FIG. 5 shows a flood map (lower portion of FIG. 5) and top (T) and side (S) views of a first setup (A) of a DOI detector device according to a first embodiment with DOI encoding. The measurement conditions included 2D encoding due to reflector foils in the outer layer, all crystals grinded on one outer side, inner layer (IL) with air gaps 21 without reflector, outer layer (OL) with reflectors 27 (in x and y direction), coupling by an optical coupling agent 26 (e.g. lightguide) of e.g. 25 μm thickness, and a single crystal of e.g. 10 mm as reference. Furthermore, a SiPM sensor 28 can be used as photo detector. As a result, a coincidence resolving time (CRT) of 325 ps+/−20 ps, a light yield of approximately 1000 photons and an energy resolution of approximately 11% were obtained. Also several TDCs per sensor die reduce dark count triggers, as the light is shared only among two SiPMs (and not 4 SiPMs). This allows equal dark count triggers (or dead time) at higher effective operation temperature which is important for system design. Furthermore, the spread of the locations allows a model verification with only two parameters. Moreover, the setup can easily be extended to a three-layer DOI.

FIG. 6 shows a flood map and top (T) and side (S) views of a second setup (B) of a DOI detector device according to a second embodiment with DOI encoding. Here, the measurement conditions included 8 crystals of e.g. 3.8 mm*3.8 mm*10 mm per die, inner layer (IL) horizontal reflector, inner layer (IL) air gap 21, outer layer (OL) vertical reflector 27, optically coupled by a lightguide 26. Again, a SiPM sensor 28 can be used as photo detector.

As a result, a CRT of 340 ps+/−20 ps, layer-independent light yield, and an energy resolution of approximately 11.5% was obtained.

The mounting complexity of the setup according to the second embodiment is comparable to the above first embodiment, but uses the asymmetry in vertical and horizontal spread to do the encoding. An extension to three-layer DOI is not possible here.

Figures 7, 8:
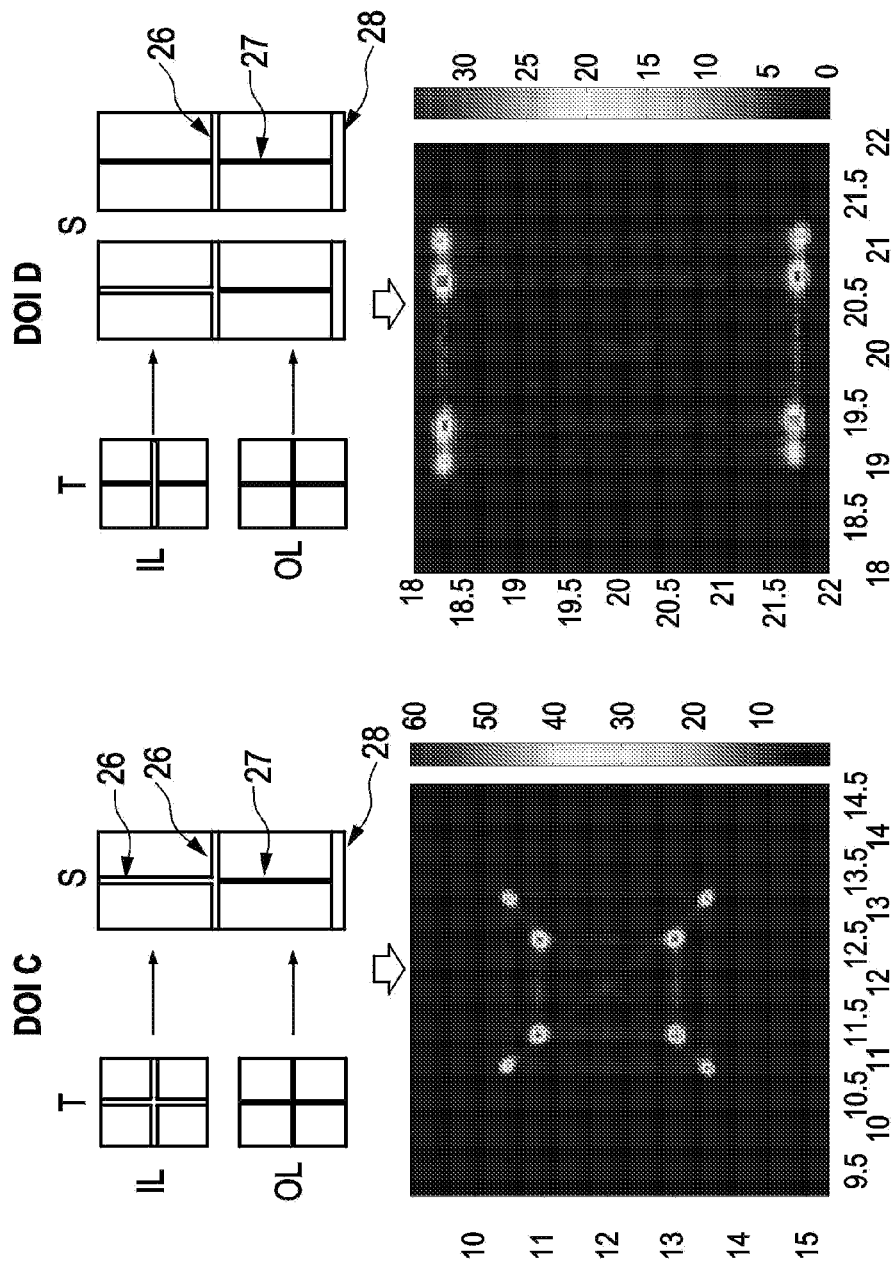
FIG. 7 shows a flood map and a setup of a DOI detector device according to a third embodiment of the present invention.
FIG. 8 shows a flood map of a setup of a DOI detector device according to a fourth embodiment of the present invention.

FIG. 7 shows a flood map and top (T) and side (S) views of a third setup (C) of a DOI detector device according to a third embodiment with DOI encoding. Here, the measurement conditions included 8 crystals of e.g. 3.8 mm*3.8 mm*10 mm per die, outer layer (OL) vertical reflectors 27, inner layer (IL) light guides 26, optically coupled by a horizontal lightguide 26. Again, a SiPM sensor 28 can be used as photo detector.

FIG. 8 shows a flood map and top (T) and side (S) views of a fourth setup (D) of a DOI detector device according to a fourth embodiment with DOI encoding. Here, the measurement conditions include 8 crystals of e.g. 3.8 mm*3.8 mm*10 mm per die, outer layer (OL) vertical reflectors 27, inner layer (IL) vertical light guide 26 and vertical reflector, optically coupled by a horizontal lightguide 26. Again, a SiPM sensor 28 can be used as photo detector.

FIG. 9 shows a flood map and top (T) and side (S) views of a fifth setup (E) of a DOI detector device according to a fifth embodiment with DOI encoding. Here, the measurement conditions included 12 crystals, e.g. 3.8 mm*2.5 mm*10 mm per die, inner layer (IL) with 3 crystals with air gaps 21 and horizontally coupled by lightguides 26, outer layer (OL) with 3 vertically-coupled crystals and vertical reflector 27 and air gaps 21, no reflector septa. A SiPM sensor 28 can be used as photo detector.

As a result, a CRT of 340 ps+/−20 ps, a light yield of approximately 1200 and an energy resolution of approximately 11% was obtained.

The setup according to the fifth embodiment realizes an effective resolution much smaller than the SiPM pitch and allows a simple separation of both layers. This setup might be sufficient for high resolution brain imaging.

FIG. 10 shows a flood map and top (T) and side (S) views of a sixth setup (F) of a DOI detector device according to a sixth embodiment with DOI encoding. Here, the measurement conditions included 8 crystals of e.g. 3.8 mm*3.8 mm*10 mm per die, inner layer (IL) with air gaps 21, outer layer (OL) with vertical reflectors 27, and optical coupling by a groove 29. Again, a SiPM sensor 28 can be used as photo detector.

Figure 11:
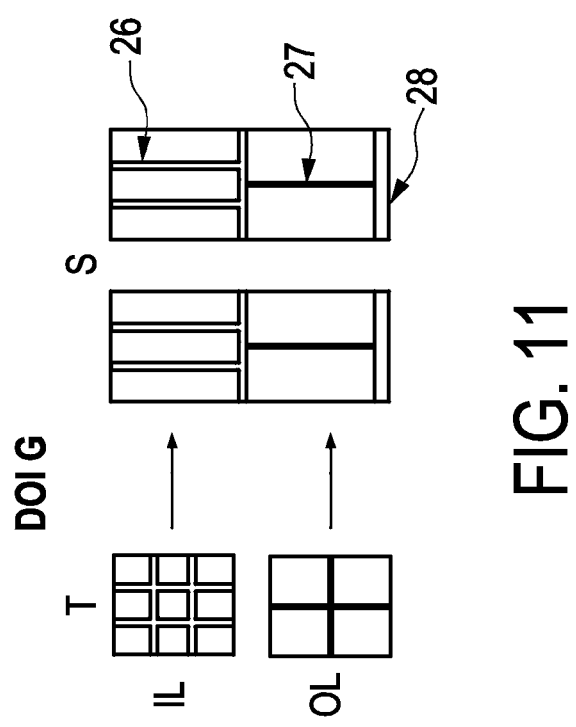
FIG. 11 shows a flood map of a setup of a DOI detector device according to a seventh embodiment of the present invention.

FIG. 11 shows a flood map and top (T) and side (S) views of a seventh setup (G) of a DOI detector device according to a seventh embodiment with DOI encoding. Here, the measurement conditions included 4+9 crystals of e.g. 10 mm with 2*2 crystals of e.g. 3.8 mm*3.8 mm*10 mm in the outer layer (OL) with reflectors 27, 3*3 crystals of e.g. 2.5 mm*2.5 mm*10 mm in the inner layer (IL), optically coupled by lightguides 26, no reflector septa. Again, a SiPM sensor 28 can be used as photo detector.

Figure 12:
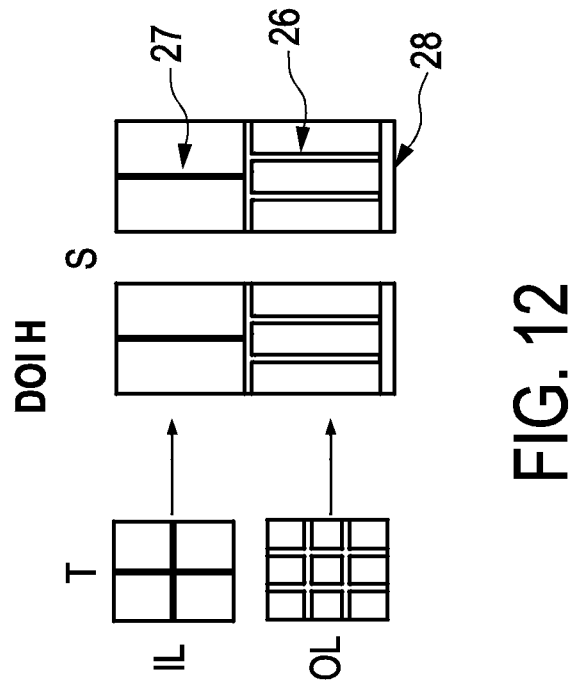
FIG. 12 shows a flood map of a setup of a DOI detector device according to an eighth embodiment of the present invention.

FIG. 12 shows a flood map and top (T) and side (S) views of an eighth setup (H) of a DOI detector device according to an eighth embodiment with DOI encoding. Here, the measurement conditions included 9+4 crystals of 10 mm with 2*2 crystals of e.g. 3.8 mm*3.8 mm*10 mm in the inner layer (IL) with reflectors 27, 3*3 crystals of e.g. 2.5 mm*2.5 mm*10 mm in the outer layer (OL), optically coupled by lightguides 26, no Reflector septa. Again, a SiPM sensor 28 can be used as photo detector.

Now, the flood map (not shown) has 9 spots from the outer layer and 4 spots from the inner layer allowing a system with effectively higher spatial resolution while maintaining optimal timing and energy resolution. This shows that smaller crystal pitch (than sensor pitch) and DOI can be combined at equal energy and timing resolution.

Figure 13:
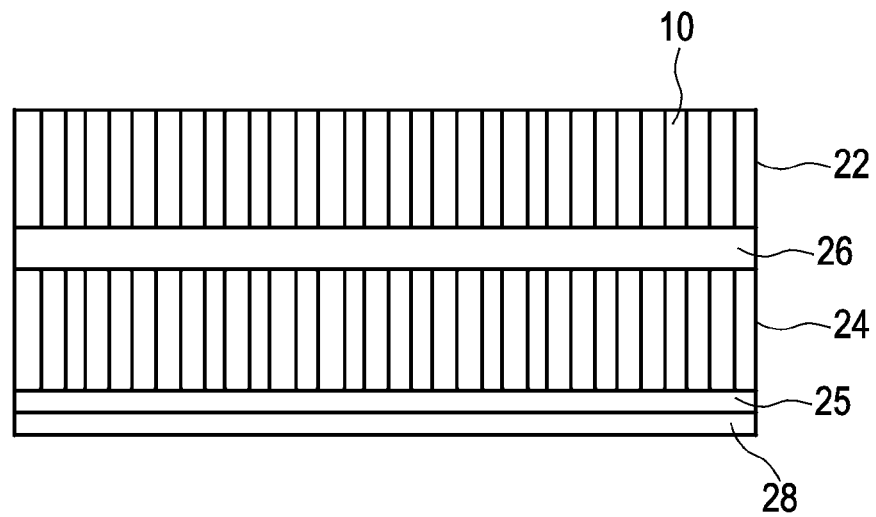
FIG. 13 shows a general construction principle of a DOI detector device according to a ninth embodiment of the present invention.

FIG. 13 shows a schematic layer structure of a DOI detector according to a ninth embodiment, where the feasibility of a two layer PET detector with single sided readout and depth encoding by the width of the light distribution is investigated. The detector is composed of two layers of scintillator arrays 22, 24 which are optically coupled by a light guide 26. Each layer is composed of 1024 (32×32) polished LYSO crystals 10 with a small pitch of about 1 mm. All side surfaces are covered with a high reflective specular reflector foil. This assembly is mounted with an additional light guide 25 onto a 64-channel dSiPM 28 array with a small pitch of about 4 mm. The width of the detector block may be about 32 mm.

To preserve the high light output and to achieve DOI information the two scintillator arrays 22, 24 are optically coupled with the light-guide 26. Thereby the light coming from the upper layer 22 is distributed broader than the light originating from the bottom layer 24. Compared to other stacked array approaches the depth encoding is solely based on the width of the light distribution instead of spatial encoding. Two measurements with the radiation source placed besides the detector array were acquired. The coincidence beam was directed into the bottom layer for the first measurement and accordingly into the top layer for the second measurement. In addition a measurement irradiating the entire detector array from the top surface was acquired. All measurements were carried out in an air conditioned laboratory environment at 21° C. The data was acquired in coincidence mode with a Na-22 radiation source. An energy weighted positioning algorithm is used to position each event. Based on the resulting flood map a single crystal is selected for detailed analysis. The dSiPM directly under the selected crystal is defined as center pixel and the adjacent eight dSiPMs are defined as neighbor pixels.

Figure 14:
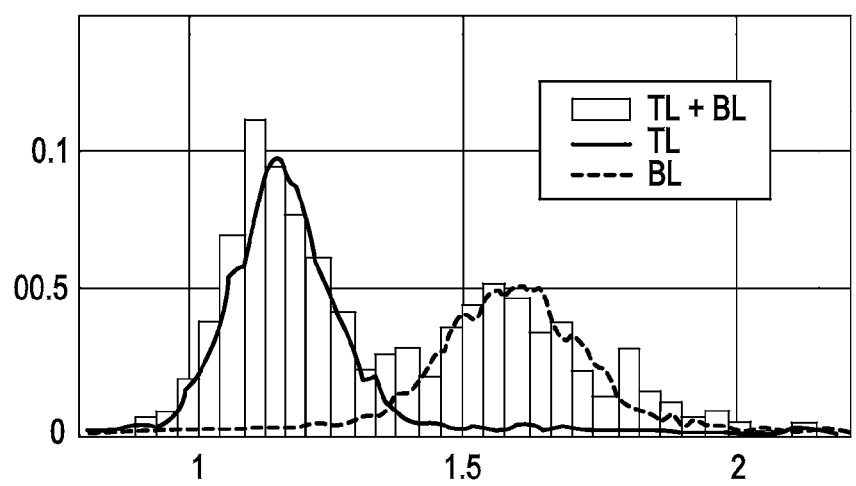
FIG. 14 shows a diagram of an energy ratio of a center pixel to neighboring pixels of the DOI detector according to the ninth embodiment.

FIG. 14 shows a diagram indicating the energy ratio of the center pixel compared to the sum of the energy of the surrounding neighbor pixels for an inner or top layer (TL), an outer or bottom layer (BL) and both layers (TL+BL) of the ninth embodiment. This ratio can be used as measure for the width of the light distribution. Here, the width of the light distribution shows two characteristic peaks whereby the individual layers can be identified.

The observed energy resolution was found to be 13% (FWHM) for 511 keV gamma rays for both layers (TL+BL). The light yield shows no considerable difference for both layers.

The DOI detector according to the above embodiments combines high light yield, good energy resolution with depth-of-interaction encoding for high resolution PET. By using dSiPMs the operation principle of the detector is insensitive to magnetic fields. Thereby the detector offers an option for high resolution detectors.

Figure 15:
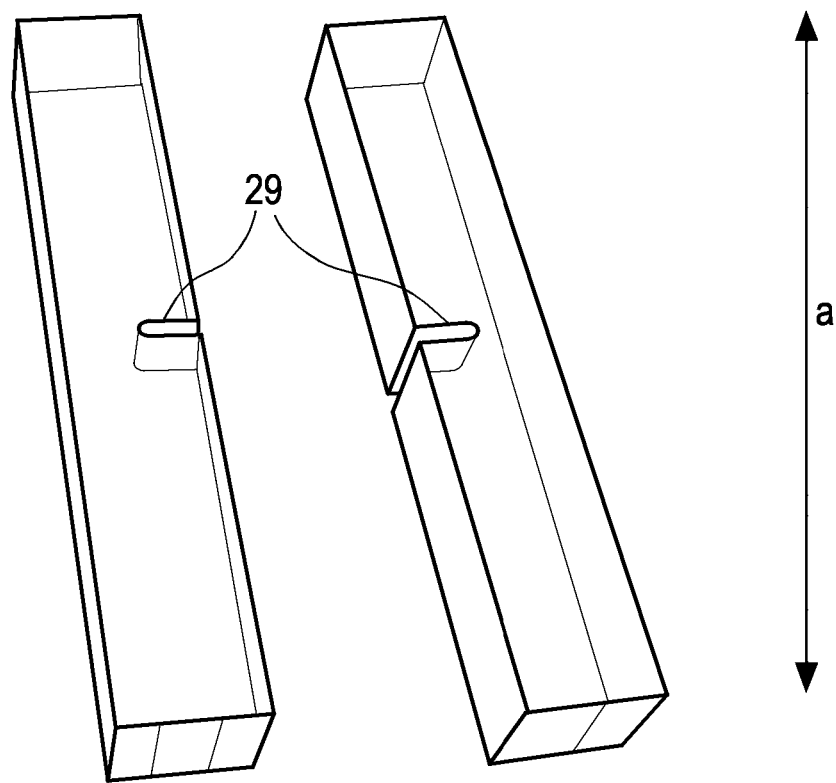
FIG. 15 shows an example of a compartment structure as used in the sixth embodiment of the present invention.

FIG. 15 shows two exemplary compartment components for respective crystals of the sixth embodiment of FIG. 10. In both components, the groove portion 29 can be seen at one side portion. As an example, the width a can be set to about 22 mm.

The optical or light tight compartments of the DOI detector may be square or rectangular at any multiple sensor pitch size (like 2*2, 2*3, 3*3, 3*4, . . . ) or independent from the sensor pitch. Furthermore, the crystal pitch in any crystal layer can be different from each other (like 2 mm in one layer and 3 mm in another layer), or the crystal pitch in any crystal layer can be different in a first (x) and second (y) direction (e.g. 2 mm in x and 3 mm in y direction). More than two crystal layers may be used in a stacked detector (e.g. 3 or 4 for example). The sensor may be connected to the top or inner crystal layer for readout. The crystal area facing the photo detector array may be rectangular (e.g. 2 mm*3 mm).

The photo detector array or sensor(s) of the DOI detector may comprise a time-to-digital converter for time stamping.

As indicated in the above embodiments, the light guides of the DOI detector may be structured for example with grooves and/or may be composed of several individual light guides. The light guides may be composed of various optically transparent materials like glass, plastic, glue with variable thickness, e.g., from μm to mm range. The scintillation crystals may themselves be structured for example with grooves and/or may be composed of several individual crystals. The grooves can be cut from one or several sides of the crystals. The surfaces of the light guides and scintillation crystals may be polished or rough, grinded, lapped, omnidirectional or scratched in certain directions on any of their faces.

As another option, the crystal arrangement of the DOI detector may be flipped, which means that it is read out by the photo detector array from the opposite side.

The positioning of the DOI detector may be based on a transfer function incorporating all energy values of the involved photo detector array or sensors. This can be based on a first moment energy weighted positioning (first moment) or second moment, or maximum likelihood positioning, etc. This positioning may be used for a crystal identification. It may make use of a coincident event of the opposite detector by making use of the incident angle. Furthermore, the identified crystal location is used for individual time skew corrections to reduce time jitter.

While the invention has been illustrated and described in detail in the drawings and foregoing description, such illustration and description are to be considered illustrative or exemplary and not restrictive; the invention is not limited to the disclosed embodiments and can be used for various imaging systems, such as PET and Single Photon Emissions Computer Tomography (SPECT) systems with CT or MR. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A detector device comprising:
   a) an assembly with a first layer of scintillation crystals for converting gamma radiation photon energy to light and a second layer of scintillation crystals for converting gamma radiation photon energy to light;
   b) a first light guide sandwiched between said second layer and said first layer and used for coupling said first and second layers so that the light coming from the second layer is distributed broader than the light originating from the first layer;
   c) a photo detector array for measuring the light generated in the scintillation crystals, said assembly being mounted with a second light guide onto said photo detector array, said second light guide being sandwiched between said photo detector array and said first layer and used for coupling said first layer and said photo detector array; and
   d) optical compartments forming a sub-structure of said scintillation crystals and covering side surfaces of said scintillation crystals by a reflective layer.

2. The device according to claim 1, further comprising light guides structured with at least one of a groove and a composition of a plurality of individual light guides.

3. The device according to claim 1, wherein the scintillation crystals comprise at least one of a groove and a composition of several individual crystals.

4. The device according to claim 1, wherein the surfaces of at least one of the light guides and the scintillation crystals are polished or rough, grinded, lapped, omnidirectional or scratched in certain directions on at least one face.

5. The device according to claim 1, wherein a pitch of said optical compartments is adapted to a sensor die pitch of said photo detector array.

6. The device according to claim 5, wherein said sensor die pitch of said photo detector array comprises a time-to-digital converter for time stamping.

7. The device according to claim 1, wherein said optical compartments are adapted to provide reflectors in a first or second direction in said second layer and no reflectors in said first layer, wherein said first direction is perpendicular to said second direction.

8. The device according to claim 1, wherein said optical compartments are adapted to provide reflectors in a first direction only in said second layer and reflectors in a second direction only in said first layer, or vice versa, wherein said first direction is perpendicular to said second direction.

9. The device according to claim 1, wherein said optical compartments are square or rectangular at any multiple sensor pitch size or independent from the sensor pitch.

10. The device according to claim 1, wherein the crystal pitch in said first layer differs from the crystal pitch in said second layer.

11. The device according to claim 1, wherein the crystal pitch in a crystal layer differs in a first and second direction and wherein said first direction is perpendicular to said second direction.

12. The device according to claim 1, where the photo detector array is connected to said first layer for readout and said first layer is an inner layer of said detector device.

13. An imaging system for imaging an object, wherein said imaging system comprises a detector device according to claim 1.

14. A detector device comprising:
- an assembly with a first layer of scintillation crystals, wherein the first layer of scintillation crystals converts gamma radiation photon energy to light, and a second layer of scintillation crystals, wherein the second layer of scintillation crystals converts gamma radiation photon energy to light;
- a first light guide sandwiched between said second layer and said first layer, wherein the first light guide couples said first and second layers so that the light coming from the second layer is distributed broader than the light originating from the first layer;
- a photo detector array, wherein the photo detector array measures the light generated in the scintillation crystals, said assembly being mounted with a second light guide onto said photo detector array, said second light guide being sandwiched between said photo detector array and said first layer, wherein the second light guide couples said first layer and said photo detector array; and
- optical compartments forming a sub-structure of said scintillation crystals and covering side surfaces of said scintillation crystals by a reflective layer.

* * * * *